(12) United States Patent
Okerlund et al.

(10) Patent No.: US 7,747,047 B2
(45) Date of Patent: Jun. 29, 2010

(54) CARDIAC CT SYSTEM AND METHOD FOR PLANNING LEFT ATRIAL APPENDAGE ISOLATION

(75) Inventors: Darin R. Okerlund, Muskego, WI (US); Jasbir S. Sra, W305 N2963 Red Oak Ct., Pewaukee, WI (US) 53072; Melissa L. Vass, Milwaukee, WI (US); Shankara B. Reddy, Cedarburg, WI (US)

(73) Assignees: GE Medical Systems Global Technology Company, LLC, Waukesha, WI (US); Jasbir S. Sra, Pewaukee, WI (US)

( * ) Notice: Subject to any disclaimer, the term of this patent is extended or adjusted under 35 U.S.C. 154(b) by 1257 days.

(21) Appl. No.: 10/249,783

(22) Filed: May 7, 2003

(65) Prior Publication Data

US 2004/0225212 A1 Nov. 11, 2004

(51) Int. Cl.
G06K 9/00 (2006.01)

(52) U.S. Cl. .................. 382/128; 382/130; 382/131; 600/407; 600/424; 600/434; 600/463; 600/467

(58) Field of Classification Search ............... 600/407, 600/424, 434, 463, 467, 523; 382/128, 130, 382/131
See application file for complete search history.

(56) References Cited

U.S. PATENT DOCUMENTS

| | | | |
|---|---|---|---|
| 3,954,098 A | 5/1976 | Dick et al. .................. 128/2.05 |
| 4,364,397 A | 12/1982 | Citron et al. |
| 4,574,807 A | 3/1986 | Hewson et al. ........ 128/419 PG |
| 5,245,287 A | 9/1993 | Nowak et al. ................ 324/322 |
| 5,274,551 A | 12/1993 | Corby, Jr. ............... 364/413.13 |
| 5,304,212 A | 4/1994 | Czeisler et al. ............... 607/88 |
| 5,348,020 A | 9/1994 | Hutson ........................ 128/696 |
| 5,353,795 A | 10/1994 | Souza et al. .............. 128/653.2 |
| 5,391,199 A | 2/1995 | Ben-Haim ................... 607/122 |
| 5,431,688 A | 7/1995 | Freeman ....................... 607/10 |
| 5,515,849 A | 5/1996 | Murashita et al. |
| 5,568,384 A | 10/1996 | Robb et al. ............ 364/419.13 |
| 5,738,096 A | 4/1998 | Ben-Haim ............... 128/653.1 |

(Continued)

FOREIGN PATENT DOCUMENTS

CN 1257693 A 6/2000

(Continued)

OTHER PUBLICATIONS

"Advanced Vessel Analysis" product descritpoin, [online] http://www.gehealthcare.com/usen/ct/clin_app/products/aswessel.html [retrieved Dec. 1, 2004].

(Continued)

*Primary Examiner*—Brian Casler
*Assistant Examiner*—Baisakhi Roy
(74) *Attorney, Agent, or Firm*—Cantor Colburn LLP

(57) ABSTRACT

A method for planning left atrial appendage (LAA) occlusion for a patient includes obtaining acquisition data from a medical imaging system, and generating a 3D model of the left atrium of the patient. One or more left atrial anatomical landmarks are identified on the 3D model, and saved views of the 3D model are registered on an interventional system. One or more of the registered saved views are visualized with the interventional system.

25 Claims, 2 Drawing Sheets

U.S. PATENT DOCUMENTS

| | | | |
|---|---|---|---|
| 5,765,561 A | 6/1998 | Chen et al. | |
| 5,823,958 A | 10/1998 | Truppe | 600/426 |
| 5,839,440 A | 11/1998 | Liou et al. | 128/654 |
| 5,951,475 A | 9/1999 | Gueziec et al. | 600/425 |
| 6,058,218 A | 5/2000 | Cline | |
| 6,081,577 A | 6/2000 | Webber | 378/23 |
| 6,154,516 A | 11/2000 | Heuscher et al. | 378/15 |
| 6,208,347 B1 | 3/2001 | Migdal | 345/419 |
| 6,233,304 B1 | 5/2001 | Hu et al. | 378/8 |
| 6,235,038 B1 | 5/2001 | Hunter et al. | 606/130 |
| 6,246,898 B1 | 6/2001 | Vesely | 600/424 |
| 6,249,693 B1 | 6/2001 | Cline et al. | 600/410 |
| 6,252,924 B1 | 6/2001 | Davantes et al. | 378/8 |
| 6,256,368 B1 | 7/2001 | Hsieh et al. | 378/8 |
| 6,266,553 B1 | 7/2001 | Fluhrer et al. | 600/428 |
| 6,275,560 B1 | 8/2001 | Blake et al. | |
| 6,289,115 B1 | 9/2001 | Takeo | 382/130 |
| 6,289,239 B1 | 9/2001 | Panescu et al. | 600/523 |
| 6,298,257 B1 * | 10/2001 | Hall et al. | 600/407 |
| 6,314,310 B1 | 11/2001 | Ben-Haim et al. | 600/424 |
| 6,325,797 B1 | 12/2001 | Stewart et al. | 606/41 |
| 6,348,793 B1 | 2/2002 | Balloni et al. | 324/309 |
| 6,353,445 B1 | 3/2002 | Babula et al. | 345/733 |
| 6,381,485 B1 | 4/2002 | Hunter et al. | 600/407 |
| 6,389,104 B1 | 5/2002 | Bani-Hashemi et al. | 378/98.12 |
| 6,411,848 B2 | 6/2002 | Kramer et al. | 607/9 |
| 6,421,412 B1 | 7/2002 | Hsieh et al. | 378/9 |
| 6,456,867 B2 | 9/2002 | Reisfeld | 600/407 |
| 6,468,265 B1 | 10/2002 | Evans et al. | 606/1 |
| 6,490,475 B1 | 12/2002 | Seeley et al. | 600/426 |
| 6,490,479 B2 | 12/2002 | Bock | 600/518 |
| 6,504,894 B2 | 1/2003 | Pan | 378/8 |
| 6,549,606 B1 | 4/2003 | Vaillant et al. | 378/4 |
| 6,556,695 B1 | 4/2003 | Packer et al. | 382/128 |
| 6,584,343 B1 | 6/2003 | Ransbury et al. | 600/509 |
| 6,650,927 B1 | 11/2003 | Keidar | 600/424 |
| 6,782,284 B1 | 8/2004 | Subramanyan et al. | 600/407 |
| 6,873,718 B2 * | 3/2005 | O'Donnell et al. | 382/131 |
| 6,889,695 B2 * | 5/2005 | Pankratov et al. | 128/898 |
| 6,928,314 B1 | 8/2005 | Johnson et al. | |
| 6,950,689 B1 | 9/2005 | Willis et al. | |
| 7,047,060 B1 | 5/2006 | Wu | |
| 7,286,866 B2 * | 10/2007 | Okerlund et al. | 600/407 |
| 7,327,862 B2 * | 2/2008 | Murphy et al. | 382/128 |
| 7,346,381 B2 * | 3/2008 | Okerlund et al. | 600/407 |
| 2002/0010392 A1 | 1/2002 | Desai | 600/374 |
| 2002/0042570 A1 | 4/2002 | Schaldach et al. | |
| 2002/0046756 A1 | 4/2002 | Laizzo et al. | 128/899 |
| 2002/0138105 A1 | 9/2002 | Kralik | 607/9 |
| 2003/0018251 A1 | 1/2003 | Solomon | 600/427 |
| 2003/0023266 A1 * | 1/2003 | Borillo et al. | 606/200 |
| 2003/0028183 A1 | 2/2003 | Sanchez et al. | 606/34 |
| 2003/0030635 A1 * | 2/2003 | Meinzer et al. | 345/419 |
| 2003/0097219 A1 | 5/2003 | O'Donnell et al. | 702/19 |
| 2003/0120264 A1 | 6/2003 | Lattouf | |
| 2003/0187358 A1 | 10/2003 | Okerlund et al. | 600/443 |
| 2003/0220557 A1 | 11/2003 | Cleary et al. | 600/409 |
| 2004/0027347 A1 | 2/2004 | Farsaie | 345/419 |
| 2004/0087850 A1 | 5/2004 | Okerlund et al. | 600/407 |
| 2004/0097806 A1 * | 5/2004 | Hunter et al. | 600/434 |
| 2004/0225328 A1 | 11/2004 | Okerlund et al. | 607/9 |
| 2004/0225331 A1 * | 11/2004 | Okerlund et al. | 607/14 |
| 2005/0080328 A1 * | 4/2005 | Vass et al. | 600/407 |

FOREIGN PATENT DOCUMENTS

| | | |
|---|---|---|
| EP | 1182619 A2 | 2/2002 |
| EP | 1321101 A2 | 12/2002 |
| JP | 1994-054843 | 3/1994 |
| JP | 2001-511031 | 8/2001 |
| JP | 2004-329939 | 11/2004 |
| WO | WO 91/07726 | 5/1991 |
| WO | 9832371 | 1/1998 |

OTHER PUBLICATIONS

"CardilQ" product description, [online], http://egems.gehealtcare.com/geCommunity/Europe/flex_trial/awFlexTrial/aw3_1/eflextrial [retrieved Dec. 1, 2004].

PCT Search Report for PCT/US2004/020909.

F. H.M. Wittkampf et al.; "Loca Lisa—New Technique for Real-Time 3-Dimensional Localization of Regular Intracardiac Electrodes;" *Circulation*h; 1999; 99: 1312-1317.

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success;" *Circulation* 1996; 94:407-24.

L. Gepstein et al., "A Novel Method for Nonfluoroscopic Catheter-Based Electroanatomical Mapping of the Heart: In Vitro and In Vivo Accuracy Results;" *Circulation* 1997; 95:1611-22.

S. Shpun et al., "Guidance of Radiofrequency Endocardial Ablation with Real-time Three-dimensional Magnetic Navigation System;" *Circulation* 1997; 96:2016-21.

J. Sra et al., "Electroanatomic Mapping to Identify Breakthrough Sites in Recurrent Typical Human Flutter;" *Paceing Clin. Electrophysiol* 2000; 23:1479-92.

R.J. Schilling et al.; "Simultaneous Endocardial Mapping in the Human Left Ventricle Using a Noncontact Catheter: Comparison of Contact and Reconstructed Electrograms During Sinus Rhythm;" *Circulation* 1998; 98:997-98.

C. C. Gornick et al., "Validation of a New Noncontact Catheter System for Electroanatomic Mapping of Left Ventricular Endocardium;" *Circulation* 1999; 99:829-835.

J. Sra et al., "Noncontact Mapping for Radiofrequency Ablation of Complex Cardiac Arrhythmias;" *J. Interven. Cardiac Electrophysiol* 2001; 5:323-331.

N. M.S. de Groot et al., "Three-Dimensional Catheter Positioning During Radiofrequency Ablation in Patients: First Application of a Real-Time Position Management System;" *J. Interven. Cardiac Electrophysiol* 2001; Nov. 11(11):1183-92.

J. Schreieck et al., "Radiofrequency Ablation of Cardiac Arrhythmias Using a Three-Dimensional Real-Time Position Management and Mapping System;" *Pacing Clin. Ekectrophysiol*, Dec. 25, 2002(12):1699-707.

F. Wittkampf et al., "Real-Time, Three-Dimensional, Nonfluoroscopic Localization of the Lasso Catheter;" *J. Interven. Cardiac Electrophysioll* 2002, 13:630.

J. Sra et al., "Cardiac Chamber Geometry Construction, Catheter Navication and Ablation Using Cutaneous Patches;" *Supplement to Circulation* Oct. 2003, 108 (17): IV-585, Abstract 2667.

J. Sra et al., "Three-Dimensional Right Atrial Geometry Construction and Catheter Tracking Using Cutaneous Patches;" *J. Interven. Cardiac Electrohysiol*, 2003 14:897.

Z. Zhang; "Iterative Point Matching for Registration of Free-Form Curves;" *Inria* 1992, pp. 1-40.

C.L. Grines et al.; "Functional Abnormalities in Isolated Left Bundle Branch Block: The Effect of Interventricular Asynchrony;" *Circulation*; 1989; 79:845-53.

H. B. Xia et al., "Differing effects of right ventricular pacing and left bundle branch block on left ventricular function;" *Br. Heart J.*, 1993; 69:166-173.

S. Cazeau et al., "Effects of Multisite Biventricular Pacing in Patients with Heart Failure and Intraventricular Conduction Delay;" *N. Engl. J. Med.* 2001; 344:873-880.

M. V. Pitzalis et al., "Cardiac Resynchronization Therapy Tailored by Echocardiographic Evaluation of Ventricular Acnchrony;" *J. Am. Coll. Cardiol.* 2002; 40:1615-22.

W. T. Abraham et al., "Cardiac Resynchronization in Chronic Heart Failure;" *N. Engl. J. Med.* 2002; 346:1845-1853.

C. A. Pelizzari et al., "Accurate Three-Dimensional Registration of CT, PET, and/or MR Images of the Brain;" *J. Comput. Assist. Tomogr.* 1989; 13:20-26.

A.C. Evans et al.; "MRI-PET Correlation in Three Dimensions Using a Volume-of-Interest (VOI) Atlas;" *J. Cerb Flow Metab.* 1991; 11:A69-A78.

R.P. Woods et al.; "Rapid Automated Algorithm for Aligning and Reslicing PET Images;" *Journal of Computer Assisted Tomography*, 1992; 16:620-633.

B.A. Ardekani et al.; "A Fully Automatic Multimodality Image Registration Algorithm;" *Journal of Computer Assisted Tomography*; 1995; 19:615-623.

L. Thurfell et al.; "Registration of Neuroimaging Data: Implementation and Clinical Applications;" *American Society of Neuroimaging*; 2000; 10:39-46.

S. A. Ben-Haim et al.; "Nonfluoroscopic, in vivo navigation and mapping technology;" *Nature Medicine*; 1996, 2:1393-5.

B. Taccardi et al.; "A new intracaitary probe for detecting the site of origin of ectopic ventricular beats during one cardiac cycle;" *Circulation*; 1987; 75:272-81.

F. H.M. Wittkampf et al.; "New Technique for Real-Time 3-Dimensional Localization of Regular Intracardiac Electrodes;" *Circulation*; 1999; 99:1312-17.

V. Fuster et al. "ACC/AHA/NASPE 2002 Guidelines Update for Implantation of Pacemakers and Antiarrhythmia Devices;"J. Am. Coll. Cardiol 2001; 38:1-47.

D. R. Ney "Volumetric Rendering of Computed Tomography Data: Principles and Techniques;" *IEEE Computer Graphics and Applications*; 1990; 24-32.

N. M. Alpert et al., "The Principal Axes Transformation—A Method for Image Registration;" *The Journal of Nuclear Medicine*; 1990; 31:1717-1722.

P.A. van den Elsen et al.; "Medical Image Matching—A Review with Classification;" *IEEE Engineering in Medicine and Biology*, 1993; 26-38.

G. T. Barnes et al.; "Conventional and Spiral Computed Tomography: Physical Principles and Image Quaility Considerations;" *Computed Body Tomography*, 1998, Lippincot-Raven, Philadelphia, PA pp. 1-20.

Milan Sonka and J. Michael Fitzpatrick (eds); *Handbook of Medical Imaging vol. 2. Medical Image Processing and Analysis*; pp. 129-174 & 447-506.

W. M. Feinberg et al.; "Prevalence, Age Distribution, and Gender of Patients with Atrial Fibrillation;" *Arch. Intern. Med.* vol. 155; Mar. 1995; pp. 469-473.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

M. Haissaguerre, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrilliation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

J. Sra et al., "Current Problems in Cardiology- Atrial Fibrilliation: Epidemiology, Mechanisms, and Management;" Current Problems in Cardiology, Jul. 2000; pp. 406-524.

ACC/AHA/ESC Practise Guidelines; Eur. Heart J., vol. 22, issue 20, Oct. 2001; pp. 1854-1923.

M. D. Leash, T. Trepelse, H. Orman, A. Bartorelli, P. Della Bella, T. Nakai, M. Reisman, D. fleschenberb, U. Krumsdorf, and D. Scherer; "Tiny Device Blocks 'Usless' Part of Heart, prevents blood clots;" Journal Report; American Heart Association; Apr. 9, 2002.

Ellen Barlow; "Operating in 3-D" found at www.med.harvard.edu/publications/HMAB/196fo3d.html.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

W. M. feinberg, J. L. Blackshear, A. Laupacis, R. Kronmal, and R. G. Hart; "Prevalence, Age Distribution, and Gender of Patients with Atrial Fibrillation;" Arch Intern Med., vol. 155, Mar. 13, 1995; pp. 469-473.

M. Haissaguerre, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrilliation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

"Current Problems in Cardiology—Atrial Fibrilliation: Epidemiology, Mechanisms, and Management;" Current Problems in Cardiology, Jul. 2000; pp. 406-524.

Barlow, Ellen. "Operating in 3-D". Harvard Medical Alumni Bulletin. Jul. 31, 2002.

Lesh, Michael D. et al. "Tiny Device Blocks 'Useless' Part of Heart, Prevents Blood Clots". American Heart Association Journal Report. Apr. 9, 2002.

Genevieve Derumeaux et al., Doppler Tissue Imaging Quantitates Regional Wall Motion During Myocardial Ischemia and Reperfusion, Circulation Journal of the American Heart Association, Circulation 1998; 97; 1970-1977.

Olivier Gerard et al., Efficient Model-Based Quantification of Left Ventricular Function in 3-D Echocardiography. IEEE Transactions on Medical Imaging, 21 (9): pp. 1059-1068, Sep. 2002.

Wahle et al., 3D Heart Vessel Reconstruction from Biplane Angiograms, IEEE Computer Graphics and Applications, 16(1): pp. 65-73, Jan. 1996.

Helmut Mair et al., Epicardial Lead Implantation Techniques for Biventricular Pacing via Left Lateral Mini-Thoracotomy, Video Assisted Thoracoscopy and Robotic Approach, The Heart Surgery Forum, 6(5): pp. 412-417, 2003.

Japanese Notice of Preliminary Rejection. Received for foreign counterpart application Aug. 4, 2009.

Second Office Action for Patent Application No. 200410038648.4; Application Date: May 8, 2004; Date of Issue: Aug. 28, 2009; 9 pgs. English Language Chinese Office Action of Chinese counterpart Application No. 200410038648.4.

Chinese Language Reference cited and discussed in English Language Chinese Office Action cited herein. Concise Statement of relevance included in English Language Chinese Office Action cited herein.

\* cited by examiner

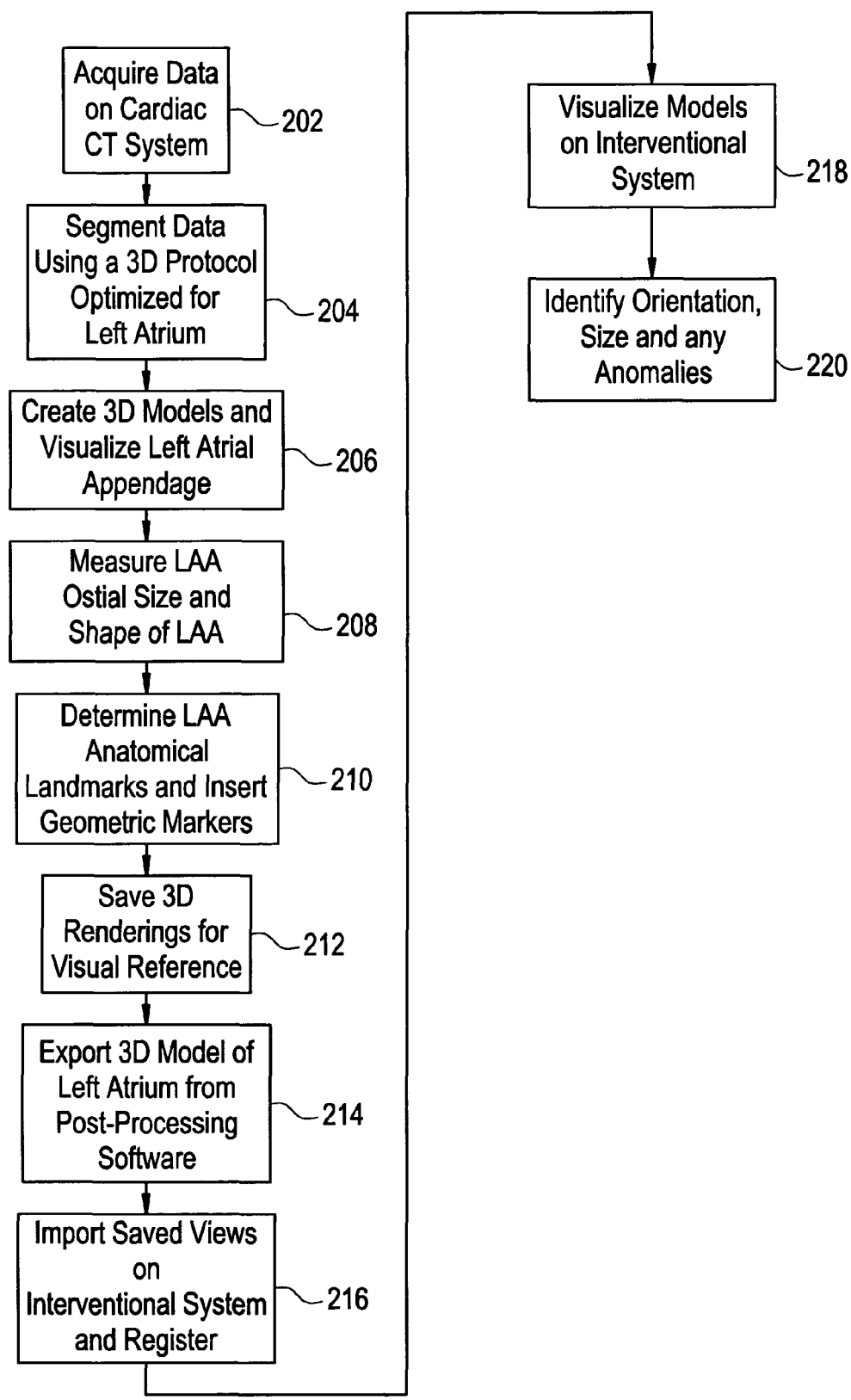

US 7,747,047 B2

CARDIAC CT SYSTEM AND METHOD FOR PLANNING LEFT ATRIAL APPENDAGE ISOLATION

BACKGROUND OF THE INVENTION

The present disclosure relates generally to cardiac implant systems and, more particularly, to a cardiac imaging system and method for planning isolation of the left atrial appendage of the heart.

Atrial fibrillation (AF) is an arrhythmia in which the atria (upper chambers of the heart) stop contracting properly as they fibrillate, and is the most common of heart rhythm irregularities. It is estimated that over 2.2 million Americans have been diagnosed with AF, with over 140,000 new cases being diagnosed each year. Patients with AF have a high risk of stroke, and about 15 percent of all strokes occur in people with atrial fibrillation. Each year, about 600,000 Americans suffer a new or recurrent stroke. In 1991, the Framingham study showed that a diagnosis of AF increased the risk of stroke 3 to 5 times higher, rising from 1.5% in the fifth decade of life to over 23% by the eighth decade.

More specifically, previous studies indicate that more than 90 percent of nonrheumatic AF-related strokes result from a blood clot that forms in the left atrial appendage (LAA), a small, thumb-shaped pouch in the heart's left upper chamber. Such clots can block a blood vessel leading to the brain, thereby causing a stroke. Several large randomized trials have shown the efficacy of warfarin, a blood thinner, in reducing the risk of stroke. In clinical practice, however, in over 40 percent of patients the drug is contraindicated or cannot be used because of the side effects, such as bleeding. Another approach to treating AF is a surgical intervention, such as the Maze procedure, in which strategic placement of incisions in both atria stops the formation and the conduction of errant electrical impulses. The maze procedure channels the normal electrical impulse to travel in one direction from the top of the heart to the bottom by producing a scar tissue that permanently blocks the travel routes of the electrical impulses that cause AF, thus eradicating the arrhythmia. In such procedures, the LAA is routinely removed, as recommended in the American College of Cardiology-American Heart Association guidelines.

Recently, in order to provide still an alternative strategy for preventing stroke, minimally invasive techniques involving deliberate occlusion of the LM are being implemented. In particular, a catheter is used to place a blocking device at the mouth of the LAA. The blocking device is a self-expanding metal cage of nitinol that pops open as the metal warms up inside the body. The cage is covered with a membrane, which blocks the atrial appendage and allows normal tissue to grow into the device. In one study of this procedure, called PLAATO (percutaneous left atrial appendage transcatheter occlusion), the patients' implants ranged in diameter from 18 to 32 millimeters with the average procedure time being 92.7 minutes. However, in 25% of those patients, the initial device was removed and replaced with one of a different size. As such, there is a need for an improved system and method for determining an effective roadmap for LAA anatomy and, where appropriate, a roadmap for effective LAA isolation and/or occlusion.

SUMMARY OF THE INVENTION

The above discussed and other drawbacks and deficiencies of the prior art are overcome or alleviated by a method for planning left atrial appendage (LM) occlusion for a patient. In an exemplary embodiment, the method includes obtaining non-invasive acquisition data from a medical imaging system, and generating a 3D model of the left atrium of the patient. One or more left atrial anatomical landmarks are identified on the 3D model, and saved views of the 3D model are registered on an interventional system. One or more of the registered saved views are visualized with the interventional system.

In another aspect, a method for planning left atrial appendage (LAA) occlusion for a patient includes obtaining acquisition data from a medical imaging system using a protocol directed toward the left atrium. The acquisition data is segmented using a 3D protocol so as to visualize the left atrium, including the LAA. A 3D model of the left atrium of the patient is generated, and one or more left atrial anatomical landmarks on the 3D model are identified. Saved views of the 3D model are registered on an interventional system, and one or more of the registered saved views are visualized on the interventional system. The orientation and size of the LM, as well as any anomalies associated therewith, are identified from the 3D model.

In still another aspect, a method for planning left atrial appendage (LAA) occlusion for a patient includes obtaining acquisition data from a cardiac imaging system such as computed tomography (CT) scanner using a protocol directed toward the left atrium. The acquisition data are segmented using a 3D protocol so as to visualize the left atrium, including the LAA. A 3D model of the left atrium of the patient is generated, and one or more left atrial anatomical landmarks on the 3D model are identified. Saved views of the 3D model are registered on a fluoroscopy system, and one or more of the registered saved views are visualized with the fluoroscopy system. The orientation and size of the LAA, as well as any anomalies associated therewith, are identified from the 3D model.

In still another aspect, a system for planning left atrial appendage (LAA) occlusion for a patient includes a medical imaging system for generating non-invasive acquisition data, and an image generation subsystem for receiving the acquisition data and generating one or more images of the left atrium of the patient. An operator console or post-processing device is configured for identifying one or more left atrial anatomical landmarks on the one or more images. The workstation includes post processing software for saving views of the 3D model that can be registered on an interventional system. The interventional system is configured for visualizing one or more of the registered saved views therewith and identifying the orientation and size of the LAA.

In still another aspect, a system for planning left atrial appendage occlusion for a patient includes a cardiac computed tomography (CT) imaging system for generating acquisition data, the CT imaging system using a protocol directed toward the left atrium. An image generation subsystem receives the acquisition data and generates one or more images of the left atrium of the patient. The image generation system is further configured for segmenting the acquisition data using a 3D protocol so as to visualize the left atrium, including the LAA. An operator console is configured for identifying one or more left atrial anatomical landmarks on the one or more images, and a workstation includes post processing software for registering saved views of the 3D model on a fluoroscopy system. The fluoroscopy system is configured for visualizing one or more of the registered saved views therewith and identifying the orientation and size of the LAA.

BRIEF DESCRIPTION OF THE DRAWINGS

Referring to the exemplary drawings wherein like elements are numbered alike in the several Figures:

FIG. 2 is a flow diagram of a method for planning left atrial appendage isolation, in accordance with a further embodiment of the invention.

DETAILED DESCRIPTION

Figure 1:
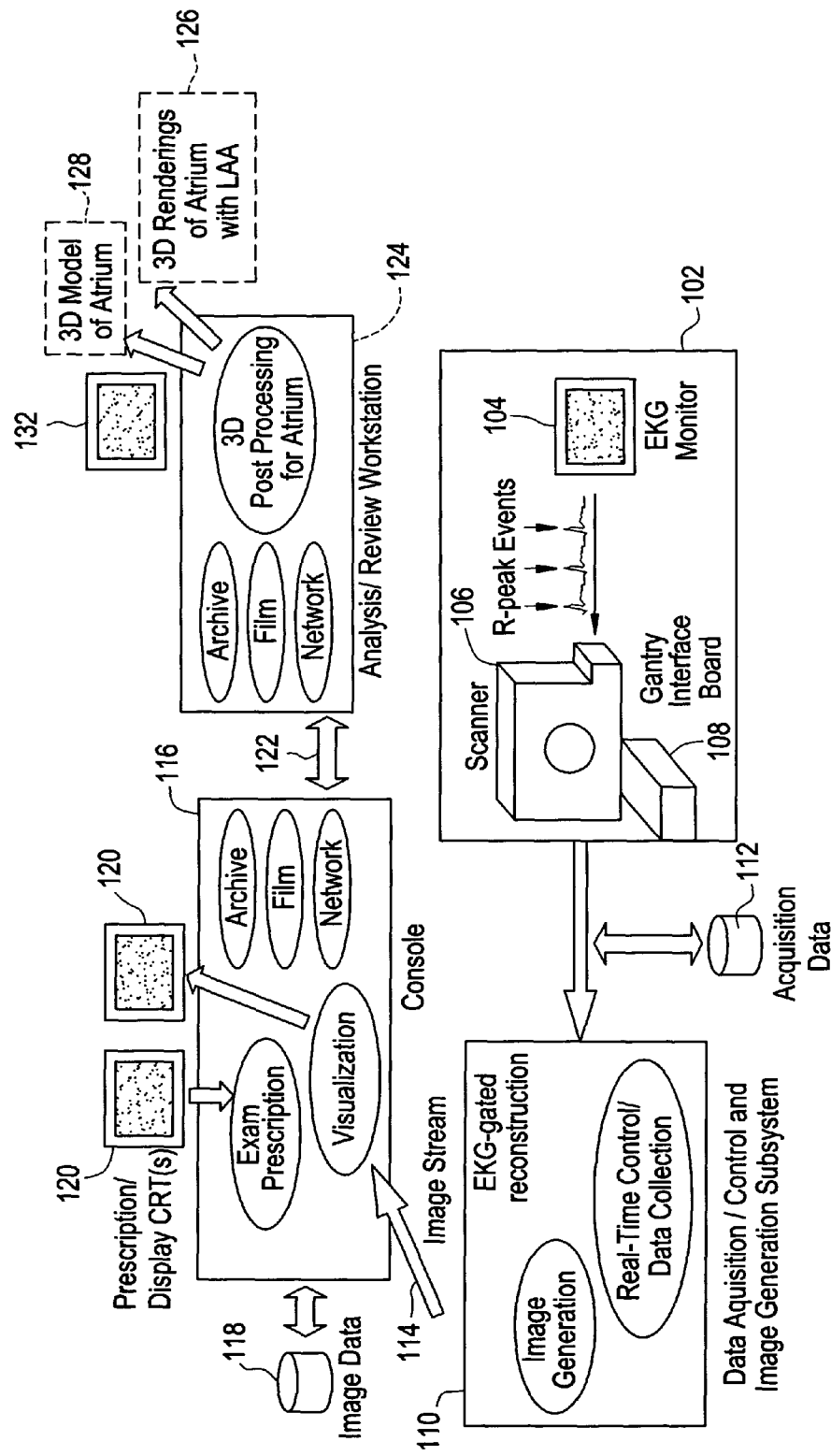
FIG. 1 is a schematic diagram of a medical imaging system, such as a computed tomography (CT) system, suitable for planning left atrial appendage isolation, in accordance with an embodiment of the invention.

Disclosed herein is a cardiac computed tomography (CT) system and method for LAA isolation/occlusion that provides information for planning interventional procedures that enable an electrophysiologist, cardiologist and/or surgeon to plan in advance a desired approach to take for the procedure. Additionally, with a more detailed three-dimensional (3D) geometrical representation of the LM, as may be obtained from imaging modalities such as CT, magnetic resonance (MR) and ultrasound, the practitioner can identify the orientation, size and any anomalies of the LM. Thus, a device or implant of the correct size may be selected during planning so as to avoid the problem of incorrectly sized implants encountered with this procedure. The 3D images obtained may also be used to plan for isolation of LAA from outside (i.e., epicardially).

Although the exemplary embodiments illustrated hereinafter are described in the context of a CT imaging system, it will be appreciated that other imaging systems known in the art are also contemplated with regard to planning LM isolation/occlusion.

Referring initially to FIG. 1, there is shown an overview of an exemplary cardiac computed tomography (CT) system 100 with support for cardiac imaging. Again, it should be understood that the cardiac CT system 100 is presented by way of example only, since other imaging systems known in the art (e.g., magnetic resonance, ultrasound) may also be used in an embodiment of the present invention. A scanner portion 102 of the system 100 includes an electrocardiographic (EKG) monitor 104 that outputs R-peak events into a scanner 106 through a scanner interface board 108. A suitable example of a scanner interface board 108 is a Gantry interface board that can be used to couple an EKG system to the scanner. The cardiac CT subsystem defined by scanner portion 102 utilizes EKG-gated acquisition or image reconstruction capabilities to image the heart free of motion in its diastolic phase, as well as in multiple phases of systole and early diastole.

Data is outputted from the scanner portion 102 into a subsystem 110 that includes software for performing data acquisition, data control and image generation. In addition, data that is outputted from the scanner 106, including R-peak time stamps, is stored in an acquisition database 112. Acquisition is performed according to one or more acquisition protocols that are optimized for imaging the heart and specifically the left atrium. Image generation is performed using one or more optimized 3D protocols for automated image segmentation of the CT image dataset for the inner surface of the LAA.

The image data stream 114 is sent to an operator console 116. The data used by software at the operator console 114 for exam prescription and visualization is stored in an image database 118, along with the data from the image data stream 114. Display screens 120 are provided to the operator of the exam prescription and visualization processes. The image data may be archived, put on film or sent over a network 122 to a workstation 124 for analysis and review, including 3D post processing. The post processing software depicted in the workstation 124 provides "immersible" views of the ostium of the LM and body of the LAA, which can be visualized from the inside. These special views can be saved and viewed by the practitioner.

The 3D protocols of the post processing software enable the software to provide the certain quantitative features of the LM, such as contour, position orientation and dimensions (e.g., circumference) of the atrium at different distances from the end of appendage, as well as between the ostia, LAA and pulmonary veins. These features may be provided automatically or semi-automatically with user input and interaction, and saved into 3D rendering files 126 for use by the practitioner for interventional planning and procedure. The post processing software also provides for the export of detailed 3D models 128 of the left atrium and LM. The 3D models 128 (which may be viewed on display screen 132 associated with workstation 124) are configured to include geometric markers inserted into the volume at landmarks of interest such that the left atrium and the LAA are visualized in a translucent fashion with the opaque geometric landmarks.

In addition, the 3D models 128 may be exported in any of several formats, including but not limited to: a wire mesh geometric model, a set of surface contours, a segmented volume of binary images, and a DICOM (Digital Imaging and Communications in Medicine) object using the radiation therapy (RT) DICOM object standard or similar object. Other formats known in the art can also be used to store and export the 3D models 128.

Referring now to FIG. 2, there is shown a flow diagram 200 illustrating a method for planning LAA isolation, in accordance with a further embodiment of the invention. Beginning at block 202, a volume of data is initially acquired on the cardiac CT system, using a protocol that is preferably optimized for the left atrium (LA) region of the heart. At block 204, the image dataset is segmented with post-processing software using a 3D protocol preferably optimized for the LA and designed to extract the surfaces of the heart chambers, including the LA. Automated procedures may be employed, where appropriate, with or without queues from the operator (e.g., location of anteroposterior, left anterior oblique, posterolateral, oblique and right anterior oblique views).

Then, as shown in block 206, the LM is visualized using 3D surface and/or volume rendering to create 3D models of the LAA, which also preferably include an immersible view (i.e., a view from the inside the chamber). In this manner, the ostial size and contour of the LAA may be measured, as is illustrated at block 208. As shown in block 210, explicit geometric markers are inserted into the volume at landmarks of interest, wherein the markers may be subsequently visualized in a translucent fashion. Then, as illustrated at block 212, specific 3D renderings and axial images (such as DICOM images, video clips, films, multimedia formats, etc.) are saved as desired for subsequent visual reference during the interventional planning and for use during the interventional procedure. The saved views are then exported and registered with the projection image on the fluoroscopy system or alternatively, with the tomosynthesis images of the 3D fluoroscopy system, as shown in block 214.

The interventional system is accessed and the imported registered models therewith are visualized by the practitioner, as shown in block 216. Finally, at block 218, the practitioner identifies the orientation, size and any anomalies of the LM such that a device or implant of the appropriate size can be selected and implanted within the LAA. It will be appreciated that automatic techniques may be employed to perform any of the above steps by using one or more of the several computer-assisted detection, localization and visualization methods available. Moreover, these methods could be completely automatic when the procedure and the organ of interest is specified or partly interactive with input from the user.

It will further be appreciated that through the use of the above described method and system embodiments, the planning of LAA occlusion is improved in that the imaging information generated and registered allows for an appropriately tailored approach to the interventional/procedure. In choosing the appropriate approach, the duration of the procedure itself is reduced and any unnecessary procedures are also eliminated. More particularly, a detailed 3D geometric representation of the LAA wall increases the precision of the isolation/occlusion procedure by providing the contour, position orientation and dimensions (e.g., circumference) of the atrium at different distances from the end of appendage, as well as between the ostia, LM and pulmonary veins. These features may be further provided automatically or semi-automatically with user input and interaction.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for planning left atrial appendage (LAA) occlusion for a patient, the method comprising:
   planning the LAA occlusion, wherein the planning includes:
      obtaining acquisition data from a medical imaging system;
      generating a 3D model of the left atrium of the patient;
      identifying one or more left atrial anatomical landmarks on said 3D model;
      inserting geometric markers within said 3D model, the geometric markers being associated with and inserted at the identified landmarks for subsequent registration;
      registering saved views of said 3D model on an interventional system; and
      visualizing one or more of said registered saved views with said interventional system.

2. The method of claim 1, further comprising identifying, from said 3D model, orientation and size of the LAA.

3. The method of claim 1, wherein said obtaining acquisition data is implemented with protocols directed for imaging the left atrium.

4. The method of claim 3, further comprising utilizing post processing software to process said acquisition data so as to generate immersible views of the ostium of the LAA.

5. The method of claim 4, wherein said 3D model and said immersible views are visualized through a display screen associated with said interventional system.

6. The method of claim 1, further comprising measuring the LAA ostial size and contour.

7. The method of claim 1, wherein the visualizing comprises visualizing the 3D model in a translucent fashion with opaque geometric markers.

8. A method for planning left atrial appendage (LAA) occlusion for a patient, the method comprising:
   planning the LAA occlusion, wherein the planning includes:
      obtaining acquisition data from a medical imaging system using a protocol directed toward the left atrium;
      segmenting said acquisition data using a 3D protocol so as to visualize the left atrium, including the LAA;
      generating a 3D model of the left atrium of the patient;
      identifying one or more left atrial anatomical landmarks on said 3D model;
      inserting geometric markers within said 3D model, the geometric markers being associated with and inserted at the identified landmarks for subsequent registration;
      registering saved views of said 3D model on an interventional system;
      visualizing one or more of said registered saved views with said interventional system; and
      identifying, from said 3D model, the orientation and size of the LAA, as well as any anomalies associated therewith.

9. The method of claim 8, further comprising utilizing post processing software to process said acquisition data so as to generate immersible views of the ostium of the LAA.

10. The method of claim 9, wherein said 3D model and said immersible views are visualized through a display screen associated with said interventional system.

11. The method of claim 8, wherein said obtaining acquisition data is EKG gated.

12. The method of claim 8, wherein said medical imaging system is one of a computed tomography system, a magnetic resonance imaging system and an ultrasound system.

13. A method for planning left atrial appendage (LAA) occlusion for a patient, the method comprising:
   planning the LAA occlusion, wherein the planning includes:
      obtaining acquisition data from a cardiac computed tomography (CT) imaging system using a protocol directed toward the left atrium;
      segmenting said acquisition data using a 3D protocol so as to visualize the left atrium, including the LAA;
      generating a 3D model of the left atrium of the patient;
      identifying one or more left atrial anatomical landmarks on said 3D model;
      inserting geometric markers within said 3D model, the geometric markers being associated with and inserted at the identified landmarks for subsequent registration;
      registering saved views of said 3D model on a fluoroscopy system;
      visualizing one or more of said registered saved views with said fluoroscopy system; and
      identifying, from said 3D model, the orientation and size of the LAA, as well as any anomalies associated therewith.

14. The method of claim 13, further comprising utilizing post processing software to process said acquisition data so as to generate immersible views of the ostium of the LAA.

15. The method of claim 14, wherein said 3D model and said immersible views are visualized through a display screen associated with said fluoroscopy system.

16. The method of claim 13, wherein said obtaining acquisition data is EKG gated.

17. A system for planning left atrial appendage (LAA) occlusion for a patient, comprising:
- a medical imaging system for generating acquisition data;
- an image generation subsystem for receiving said acquisition data and generating one or more images of the left atrium of the patient;
- an operator console for identifying one or more left atrial anatomical landmarks on said one or more images and for inserting geometric markers onto said one or more images, the geometric markers being associated with and inserted at the identified landmarks for subsequent registration; and
- a workstation including post processing software configured to plan the LAA occlusion including registering saved views of said one or more images on an interventional system;
- wherein said interventional system is configured for visualizing one or more of said registered saved views therewith and identifying the orientation and size of the LAA.

18. The system of claim 17, wherein said image generation subsystem is configured with protocols directed for imaging the left atrium.

19. The system of claim 18, wherein said post processing software is further configured to process said acquisition data so as to generate immersible views of the ostium of the LAA.

20. The system of claim 19, further comprising a display screen associated with said interventional system, said display screen for visualizing said 3D model and said immersible views.

21. The System of claim 17, wherein said interventional system is configured for visualizing one or more of said registered saved views comprising images of the left atrium in a translucent fashion with opaque geometric markers.

22. A system for planning left atrial appendage (LAA) isolation for a patient, comprising:
- a cardiac computed tomography (CT) imaging system for generating acquisition data, said CT imaging system using a protocol directed toward the left atrium;
- an image generation subsystem for receiving said acquisition data and generating one or more images of the left atrium of the patient;
- said image generation system further configured for segmenting said acquisition data using a 3D protocol so as to visualize the left atrium with a 3D model, including the LAA;
- an operator console for identifying one or more left atrial anatomical landmarks on said 3D model and for inserting geometric markers within said 3D model, the geometric landmarks being associated with and inserted at the identified landmarks for subsequent registration; and
- a workstation including post processing software configured to plan the LAA occlusion including registering saved views of said 3D model on a fluoroscopy system;
- wherein said fluoroscopy system is configured for visualizing one or more of said registered saved views therewith and identifying the orientation and size of the LAA.

23. The system of claim 22, wherein said post processing software is further configured to process said acquisition data so as to generate immersible views of the ostium of the LAA.

24. The system of claim 23, further comprising a display screen associated with said fluoroscopy system, said display screen for visualizing said 3D model and said immersible views.

25. The system of claim 22, wherein said image generating subsystem is EKG gated.

* * * * *